United States Patent
Liu et al.

(10) Patent No.: US 11,337,794 B2
(45) Date of Patent: May 24, 2022

(54) INTRAOCULAR LENS HAVING A HAPTIC STRUCTURE WITH A STREAMLINED CROSS-SECTIONAL GEOMETRY

(71) Applicant: Alcon Inc., Fribourg (CH)

(72) Inventors: Jian Liu, Keller, TX (US); Stephen J. Van Noy, Southlake, TX (US)

(73) Assignee: Alcon Inc., Fribourg (CH)

( * ) Notice: Subject to any disclaimer, the term of this patent is extended or adjusted under 35 U.S.C. 154(b) by 86 days.

(21) Appl. No.: 16/174,409

(22) Filed: Oct. 30, 2018

(65) Prior Publication Data
US 2019/0125521 A1 May 2, 2019

Related U.S. Application Data

(60) Provisional application No. 62/579,989, filed on Nov. 1, 2017.

(51) Int. Cl.
*A61F 2/16* (2006.01)

(52) U.S. Cl.
CPC ........ *A61F 2/16* (2013.01); *A61F 2002/1681* (2013.01); *A61F 2002/1683* (2013.01); *A61F 2002/16901* (2015.04); *A61F 2210/0076* (2013.01)

(58) Field of Classification Search
CPC ............... A61F 2/16; A61F 2002/1681; A61F 2002/1683; A61F 2002/1686; A61F 2002/16901
See application file for complete search history.

(56) References Cited

U.S. PATENT DOCUMENTS

| | | | |
|---|---|---|---|
| 6,241,777 B1* | 6/2001 | Kellan | A61F 2/16 623/6.51 |
| 2008/0077238 A1* | 3/2008 | Deacon | A61F 2/1613 623/6.16 |
| 2009/0076603 A1* | 3/2009 | Avery | A61F 2/1613 623/6.43 |
| 2009/0234449 A1 | 9/2009 | Juan, Jr. et al. | |
| 2010/0106245 A1* | 4/2010 | Rombach | A61F 2/1613 623/6.39 |

FOREIGN PATENT DOCUMENTS

| | | |
|---|---|---|
| FR | 2922096 A1 | 4/2009 |
| WO | 01/17461 A1 | 3/2001 |
| WO | 2008/108525 A1 | 9/2008 |
| WO | 2016/160178 A1 | 10/2016 |

* cited by examiner

*Primary Examiner* — Leslie Lopez
(74) *Attorney, Agent, or Firm* — Patterson + Sheridan, LLP

(57) ABSTRACT

An ophthalmic device includes an optic and a haptic structure coupled with the optic. The optic includes an optic axis. The haptic structure is coupled to the optic. The haptic structure retains the ophthalmic device within a capsular bag of a patient's eye. At least a portion of the haptic structure has a cross-section and a peripheral surface forming an outer periphery of a portion of the cross-section. At least a portion of the peripheral surface contacts the capsular bag and is smoothly curved.

9 Claims, 5 Drawing Sheets

INTRAOCULAR LENS HAVING A HAPTIC STRUCTURE WITH A STREAMLINED CROSS-SECTIONAL GEOMETRY

FIELD

The present disclosure relates generally ophthalmic lenses and, more particularly, to intraocular lenses having a haptic structure with a streamlines cross-sectional geometry.

BACKGROUND

Intraocular lenses (IOLs) may be implanted in patients' eyes to replace a patient's natural lens. An IOL typically includes (1) an optic that corrects the patient's vision (e.g., typically via refraction or diffraction), and (2) haptics that constitute support structures that hold the optic in place within the patient's eye (e.g., within capsular bag). In general, a physician selects an IOL for which the optic has the appropriate corrective characteristics for the patient. During ophthalmic surgery, often performed for conditions such as cataracts, the surgeon implants selected IOL by making an incision in the capsular bag of the patient's eye (a capsulorhexis) and inserting the IOL through the incision. Typically, the IOL is folded for insertion into the capsular bag via a corneal incision and unfolded once in place within the capsular bag. During unfolding, the haptics may expand such that a small section of each bears on the capsular bag, retaining the IOL in place.

In some cases, the IOL must be removed, or explanted. To explant an IOL, the IOL may be cut into small pieces and removed through an incision. The IOL may also be repositioned during the surgical procedure after the haptics have been expanded. In either explantation or repositioning of the IOL, the haptics are moved away from the capsular bag. However, because the haptics may adhere to the capsular bag, movement of the haptics may damage or tear the capsular bag. Such an injury to the patient is undesirable.

Even if the IOL remains in place, there may be shortcomings. IOLs may cause striae, or folds, in the posterior capsular bag. Striae in the capsular bag may result in posterior capsular opacification (PCO) by providing a mechanism for the growth and/or migration of cells. A mechanism for addressing PCO is thus desired.

Accordingly, what is needed is an improved IOL that may address PCO while allowing for repositioning and explantation of the IOL.

SUMMARY

In certain embodiments, an ophthalmic device includes an optic and a haptic structure coupled with the optic. The optic includes an optic axis. The haptic structure is coupled to the optic. The haptic structure retains the ophthalmic device within a capsular bag of a patient's eye. At least a portion of the haptic structure has a cross-section and a peripheral surface forming an outer periphery of a portion of the cross-section. At least a portion of the peripheral surface contacts the capsular bag and is smoothly curved.

In certain embodiment, the hatpic geometry described herein may provide one or more technical advantages. For example, IOLs having the haptic geometry described herein may be more easily explanted and/or repositioned as compared with existing IOLs.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

The skilled person in the art will understand that the drawings, described below, are for illustration purposes only. The drawings are not intended to limit the scope of the applicant's disclosure in any way.

DETAILED DESCRIPTION

The exemplary embodiments relate to ophthalmic devices such as intraocular lenses (IOLs). The following description is presented to enable one of ordinary skill in the art to make and use the invention and is provided in the context of a patent application and its requirements. Various modifications to the exemplary embodiments and the generic principles and features described herein will be readily apparent. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. Thus, the present invention is not intended to be limited to the embodiments shown, but is to be accorded the widest scope consistent with the principles and features described herein.

In general, the present disclosure relates to an ophthalmic device that includes an optic and a haptic structure coupled with the optic. The optic includes an optic axis. The haptic structure is coupled to the optic. The haptic structure retains the ophthalmic device within a capsular bag of a patient's eye. At least a portion of the haptic structure has a cross-section and a peripheral surface forming an outer periphery of a portion of the cross-section. At least a portion of the peripheral surface contacts the capsular bag and is smoothly curved.

Figure 1A:
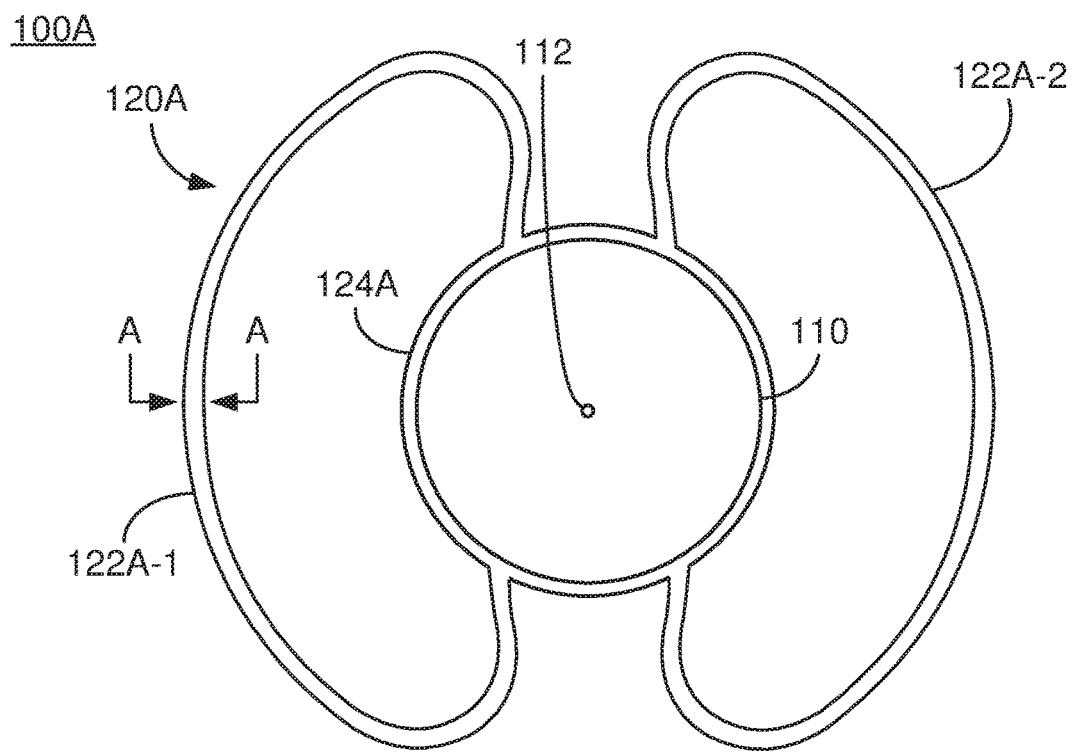
FIGS. 1A-1I depict various views of an exemplary embodiment of an ophthalmic device having a haptic structure with a cross-section having a streamlined periphery.
Figure 1B:
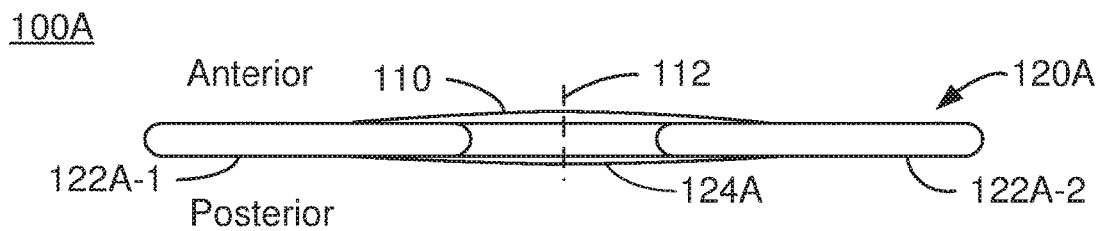
Figure 1C:
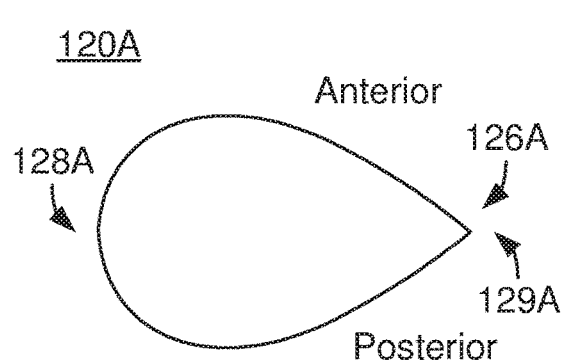
Figure 1D:
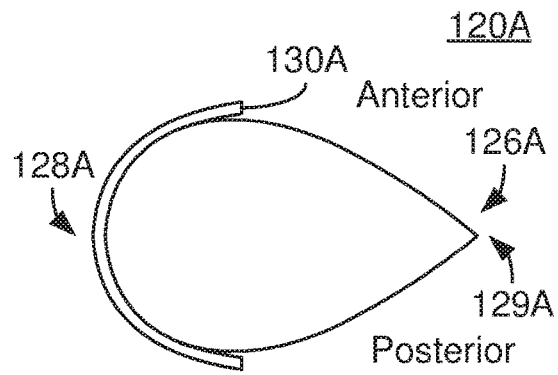
Figure 1E:
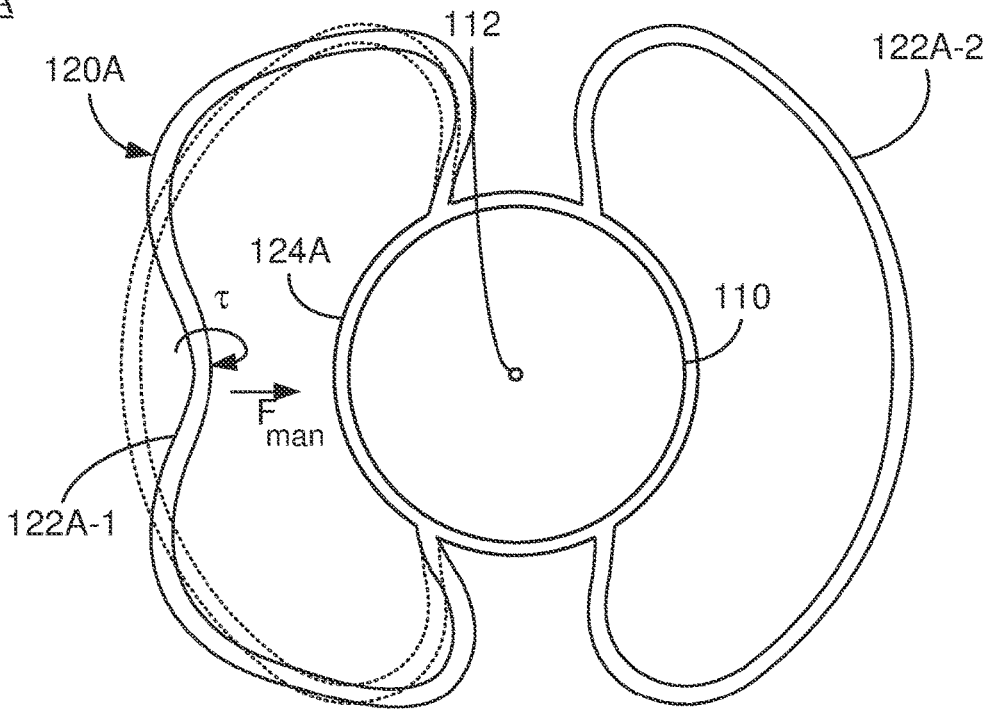
Figure 1F:
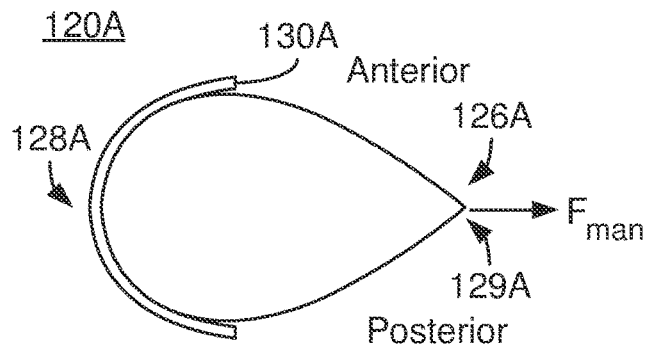
Figure 1G:
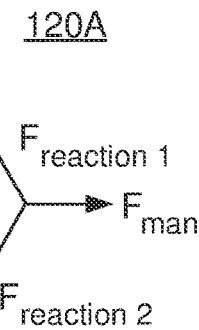

FIGS. 1A-1G depict various views of an exemplary embodiment of an ophthalmic device 100A having a closed-loop haptic structure 120A with a cross-section having a streamlined periphery. As discussed below, in other embodiments, an open-loop haptic structure may be used. For simplicity, the ophthalmic device 100A is also referred to as an IOL 100A. For clarity, FIGS. 1A-1G are not to scale and not all components may be shown. The IOL 100A includes the haptic structure 120A as well as an optic 110. FIGS. 1A and 1B are plan and side views of the IOL 100A. FIG. 1C is a cross-sectional view of a portion of the haptic structure 120A. FIG. 1D is a cross-sectional view of the portion of the haptic structure 120A when in use in a patient's eye. FIG. 1E is a plan view of the IOL 100A when being manipulated. FIG. 1F is a cross-sectional view of a portion of the haptic structure 120A when being manipulated. FIG. 1G depicts the forces involved in manipulating the haptic structure 120A.

The optic 110 is an ophthalmic lens 110 that may be used to correct a patient's vision. For example, the optic may be a refractive and/or diffractive lens. The optic 110 may be a monofocal lens, a multifocal lens, a toric lens, accommodating or another, analogous lens. The anterior and/or posterior surface of the optic 110 may thus have features including but not limited to a base curvature and diffraction grating(s). The optic 110 may refract and/or diffract light to correct the patient's vision. The optic 110 has an optic axis 112 that is out of the plane of the page in FIG. 1A. The optic 110 is depicted as having a circular footprint in the plan view of FIG. 1A. In other embodiments, the optic 110 may have a differently shaped footprint. In some embodiments, the optic 110 may also include other features that are not shown for clarity. The optic 110 may be formed of one or more of a variety of flexible optical materials. For example, the optic 110 may include but is not limited to one or more of silicone, a hydrogel and an acrylic such as AcrySof®.

The haptic structure 120A is a support structure used to hold the ophthalmic device 100A in place in the capsular bag of a patient's eye (not explicitly shown in FIGS. 1A-1C and 1E). A portion of the capsular bag 130A is shown in FIG. 1D. The haptic structure 120A includes closed loops 122A-1 and 122A-2 (collectively 122) and inner ring or frame 124A. The inner portion of the frame 124A is desired to match the shape of the optic 110. In other embodiments, the frame 124A may be omitted. In some embodiments, the haptic structure 120A and the optic 110 may be molded together. Thus, the optic 110 and haptic 120A may form a single monolithic structure. In other embodiments, the haptic structure 120A may be otherwise attached to the optic 110. For example, the haptic structure 120A may be bonded to or molded around a preexisting optic 110.

Figure 1H:
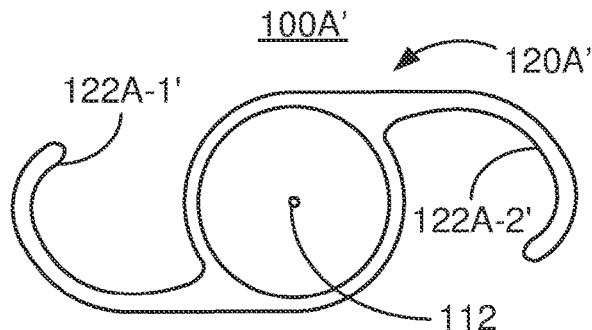
Figure 1I:
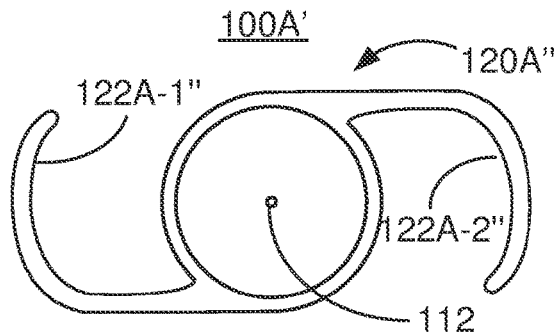

The loops 122A retain the IOL 100A in position in the patient's eye by bearing upon the capsular bag 130A. Each of the loops 122A subtends a large angle. Consequently, the loops 122A contact the capsular bag over a significantly larger angle than for haptics having open loops. As a result, stability may be enhanced and formation of striae reduced. Although two closed loops 122A are shown, another number of loops may be used. The shape of the closed loops 122A may differ. Further, open loops rather than closed loops may be used in other embodiments. For example, FIGS. 1H and 1I depict IOLs 100A' and 100A" analogous to the IOL 100A. FIG. 1H depicts an IOL 100A' having C-shaped open loops 122A-1' and 122A-2' (collectively loops 122A'). FIG. 1I depicts an IOL 100A" having L-shaped open loops 122A-1" and 122A-2". Thus, the IOLs 100A' and 100A" may be the same as the IOL 100A except that the loops 122A' and 122A" are open. For example, the cross-section of the open loops 122A' and 122A" may be the same as the cross section for closed loops 122A.

FIGS. 1C and 1D depict the cross-section of the closed loops 122A, for example at the line A-A shown in FIG. 1A. Although a specific location for the cross-section is shown in FIG. 1A, in other embodiments, the cross-section may be the same at another portion of the closed loop 122A-1 and/or for at least part of the other closed loop 122A-2. The cross-section shown in FIGS. 1C-1D is for at least part of the loop(s) 122A that bear on the capsular bag. In some embodiments, the entirety of each loop 122A has the cross-section shown. In other embodiments, the portion of a loop 122A that does not bear on the capsular bag 130A, for example near the frame 124A, may have a different cross-section.

The cross-section for the loop(s) 122A has an inner peripheral surface 126A and an outer peripheral surface 128A. The outer peripheral surface 128A is at the outside of the loops 122A and may bear on the capsular bag 130A, as shown in FIG. 1D. The outer peripheral surface 128A exerts a force on the capsular bag 130A. Thus, the outer peripheral surface may aid in expanding the capsular bag 130A and stabilizing the IOL 100A within the capsular bag 130A. The inner peripheral surface 126A is opposite to the outer peripheral surface 128A and forms the inside of the loops 122A. Thus, at least part of the inner peripheral surface 126A may not contact the capsular bag or may exert significantly less force on the capsular bag. If arms rather than loops are present in the haptic structure 120A, then the inner peripheral surface forms the portion of the cross-section that does not bear on the capsular bag.

The particular shape of the cross-section may differ in different embodiments even when the general shape does not change. For example, the length between the corner 129A of the inner peripheral surface 126A and outer peripheral surface 128A and the thickness between the posterior and anterior surfaces, may differ in different embodiments. in some embodiments, the thickness may be on the order of 0.5 mm. In some such embodiments, the length may be approximately 0.9 mm. In other such embodiments, the length may be approximately 0.7 mm. Thus, the cross section of the haptic 120A may have a different appearance for different aspect ratios.

At least part of the outer peripheral surface 128A is smoothly curved. In the embodiment shown, the entire peripheral surface 128A is curved. Stated differently, the geometry for the outer peripheral surface 128A of the cross-section is streamlined. Thus, on a macro-scale, the outer peripheral surface 128A has a continuous and well-defined slope. In the embodiment shown in FIGS. 1A-1D, no additional textures or features are present on the outer peripheral surface. Textures may have a characteristic length on the order of nanometers to microns or less. Features may have a characteristic length on the order of tens of microns. In other embodiments, such textures or features may be present. However, on the scale of the diameter or height of the cross-section, the outer peripheral surface 128A is smoothly curved. Because of its curved shape, the outer peripheral surface 128A may have a greater contact with the capsular bag 130A. This is shown in FIG. 1D. As a result, the haptic 120A may be better able to stabilize the IOL 100A. In addition, the curvature of and lack of sharp corners in the outer peripheral surface 128A may make the loops 122A less likely to adhere to and tear the capsular bag 130A in the event of explantation or repositioning.

For example, FIGS. 1E and 1F depict the IOL 100A and haptic 120A when being repositioned or explanted using a manipulation force, $F_{man}$. FIG. 1G depicts a plan view of the forces involved in repositioning or explanting the IOL 100A. The manipulation force, $F_{man}$, is used in moving the haptic away from the capsular bag 130A. In response to the manipulation force, the loop 122A-1 is deformed as shown in FIG. 1E. More specifically, the portion of the loop 122A-1 to which the manipulation force is applied moves in the direction of the force: toward the optic 110. The reaction forces, $F_{reaction\ 1}$ and $F_{reaction\ 2}$, due to the manipulation force are along the loop 122A-1 and in the opposite direction to the manipulation fore. Thus, as can be seen in FIG. 1G, the reaction forces tend to separate the loop 122A-1 from the capsular bag. In addition, the loop 122A-1 also undergoes a torque, τ. This torque also tends to separate the loop 122A-1 from the capsular bag 130A. Consequently, the configuration of the cross-section of the loops 122A tend to improve the mobility of the loop 122A with respect to the capsular bag 130A when the loop 122A is being manipulated.

In contrast to the outer peripheral surface 128A, the inner peripheral surface may not be smoothly curved. In the embodiment shown, the inner peripheral surface 126A has a sharp corner 129A. On a macro-scale the slope of the inner peripheral surface 126A is not well-defined at the corner 129A and is not continuous on either side of the corner 129A. Thus, the cross-section for the haptic structure 120A is teardrop shaped. Because of the presence of the sharp corner 129A, the optic 110 may be surrounded on all sides by sharp edges. These sharp edges may also reduce the probability of cells migrating to the optic 110 from any side. PCO may be reduced or eliminated.

The frame 124A may also have sharp outside corners (at the outer surface of the frame 124A). The optic 110 might have sharp corners (not shown). As a result, the optic 110 may be surrounded on all sides by sharp edges. These sharp edges may also reduce the probability of cells migrating to the optic 110 from any side. PCO may be reduced or eliminated.

The IOL 100A may improve patient outcomes. The streamlined outer peripheral surface 128A of the cross-section of the loops 122A may reduce adherence of the loops 122A to the capsular bag 130A during explantation and/or repositioning. Thus, damage to the patient's eye due to manipulation of the haptic 120A may be reduced. The smooth curve for the outer peripheral surface 128A may also allow for improved stability of the IOL 100A when the IOL 100A is in place. Sharp edges such as the edge 129A for the haptic structure 120A may further reduce PCO. Thus, performance of the IOL 100A may be improved.

Figure 2A:
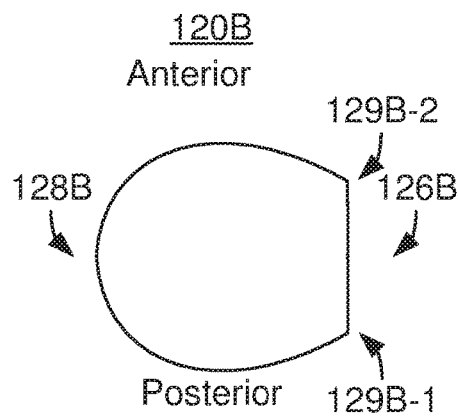
FIGS. 2A-2B depict another exemplary embodiment of a portion of an ophthalmic device having a haptic structure with a cross-section having a streamlined periphery.
Figure 2B:
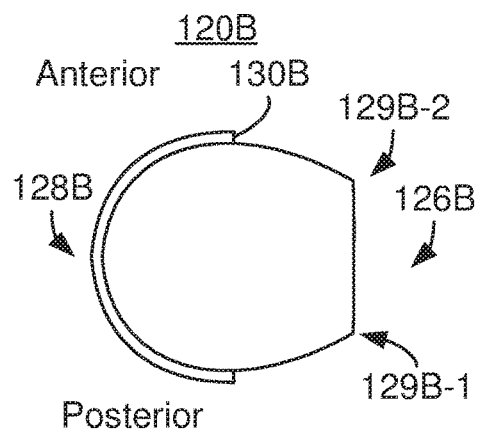

FIGS. 2A and 2B depict another exemplary embodiment of a haptic structure 120B for an ophthalmic device such as an IOL. For clarity, FIGS. 2A and 2B are not to scale and not all components may be shown. FIG. 2A depicts a cross-section of the haptic structure 120B. FIG. 2B depicts the cross-section of the haptic structure 120B when in use, bearing upon the capsular bag 130B of a patient's eye. The haptic 120B and IOL of which it is a part are analogous to the haptic 120A and IOL 100A. Consequently, analogous components have similar labels. Thus, the IOL would include an optic (not explicitly shown) and the haptic structure 120B (of which only the cross-section is shown) that are analogous to the optic 110 and the haptic structure 120A. In some embodiments, the haptic structure 120B is a closed-loop haptic structure having loops analogous to the loops 122A and optionally including a frame analogous to the frame 124A. The frame may be omitted, loop(s) of another size and/or another number of loops may be used. In other embodiments, the haptic structure 120B may have one or more open loops.

The haptic structure 120B functions in an analogous manner to and shares analogous benefits with the haptic structure 120A. The haptic structure 120B thus includes an outer peripheral surface 128B and an inner peripheral surface 126B that are analogous to surfaces 128A and 126A, respectively. However, the shape of the cross-section is different. The entire peripheral surface 128B is smoothly curved. Thus, on a macro-scale, the outer peripheral surface 128B has a continuous and well-defined slope. In the embodiment shown in FIGS. 2A-2B, no additional textures or features are present on the outer peripheral surface 128B. In another embodiment, textures, features, and/or a coating may be present on the IOL 100B. Because of its curved shape, the outer peripheral surface 128B may have a greater contact with the capsular bag 130B as shown in FIG. 2B. As a result, the haptic 120A may be better able to stabilize the IOL 100A. In addition, the curvature of and lack of sharp corners in the outer peripheral surface 128B may make the loops less likely to adhere to and tear the capsular bag 130A in the event of explantation or repositioning.

Instead of having a teardrop shape, most of the peripheral surface 126B is flat. Thus, the inner peripheral surface 126B includes a straight side and two sharp corners 129B-1 and 129B-2. On a macro-scale the slope of the inner peripheral surface 126B is not well-defined at the corners 129B-1 and 129B-2 and is not continuous on either side of the corners 129B-1 and 129B-2. Because of the presence of the sharp corners 129B-1 and 129B-2, the optic (not shown) may be surrounded by sharp edges on the posterior side to reduce or prevent PCO. The optic may also have a curved edge profile for glare reduction. The haptic cross-sectional edge profile may be blended and smoothly transitioned to the optic edge profile.

The haptic structure 120B may improve patient outcomes. The streamlined outer peripheral surface 128B of the cross-section may reduce adherence of the haptic structure 120B to the capsular bag 130B during explantation and/or repositioning. Thus, damage to the patient's eye due to manipulation of the haptic 120B may be reduced. The smooth curve for the outer peripheral surface 128B may also allow for improved stability of the IOL when the IOL is in place. Sharp edges such as the edges 129B-1 for the haptic structure 120B may further reduce PCO. Thus, performance of the IOL may be improved.

Figure 3A:
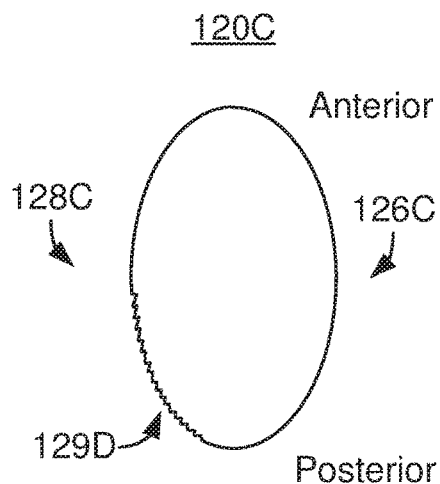
FIGS. 3A-3B depict another exemplary embodiment of a portion of an ophthalmic device having a haptic structure with a cross-section having a streamlined periphery.
Figure 3B:
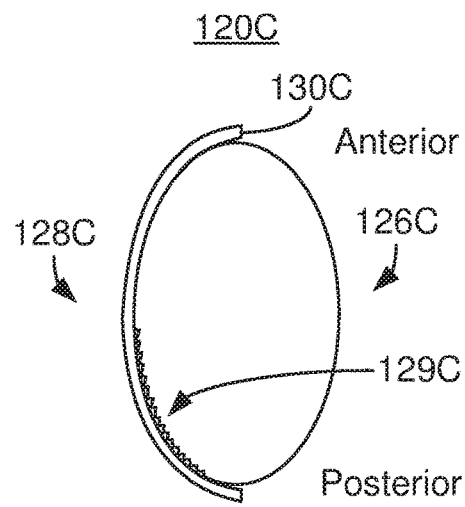

FIGS. 3A and 3B depict another exemplary embodiment of a haptic structure 120C for an ophthalmic device such as an IOL. For clarity, FIGS. 3A and 3B are not to scale and not all components may be shown. FIG. 3A depicts a cross-section of the haptic structure 120C. FIG. 3B depicts the cross-section of the haptic structure 120C when in use, bearing upon the capsular bag 130C of a patient's eye. The haptic 120C and IOL of which it is a part are analogous to the haptic(s) 120A and/or 120B. Consequently, analogous components have similar labels. Thus, the IOL would include an optic (not explicitly shown) and the haptic structure 120C that are analogous to the optic 110 and haptic structure 120A and/or 120B. In some embodiments, the haptic structure 120B is a closed-loop haptic structure having loops analogous to the loops 122A and optionally including a frame analogous to the frame 124A. The frame may be omitted, loop(s) of another size and/or another number of loops may be used. In other embodiments, the haptic structure 120C may have one or more open loops.

The haptic structure 120C functions in an analogous manner to and shares analogous benefits with the haptic structure(s) 120A and/or 120B. The haptic structure 120C thus includes an outer peripheral surface 128C and an inner peripheral surface 126C that are analogous to surfaces 128A/128B and 126A/126B, respectively. However, the shape of the cross-section is different. The entire outer peripheral surface 128B and inner peripheral surface 126C are smoothly curved.

In the embodiment shown in FIGS. 3A-3B, an additional texture or feature 129C is present on the posterior of the outer peripheral surface 128C. Whether the component 129C is a texture or feature depends upon its characteristic size, discussed above. This texture is shown as a step pattern. However, other patterns are possible. For example, a repeated wavy surface, repeated lines, or other texture or feature may be present. In another embodiment, the feature 129C may simply be a roughening of the surface. In some embodiments, textures, features, and/or a coating may be present on the IOL to help reduce PCO. Because of its curved shape, the outer peripheral surface 128C may have a greater contact with the capsular bag 130C. As a result, the haptic 120C may be better able to stabilize the IOL. In addition, the curvature of and lack of sharp corners in the outer peripheral surface 128AC may make the loops 122AC less likely to adhere to or tear the capsular bag 130A in the event of explantation or repositioning.

The haptic structure 120C may have enhanced performance. The streamlined outer peripheral surface 128C of the cross-section may reduce adherence of the haptic structure 120C to the capsular bag 130C during explantation and/or repositioning. Thus, damage to the patient's eye due to manipulation of the haptic 120C may be reduced. The smooth curve for the outer peripheral surface 128C may also allow for improved stability of the IOL when the IOL is in place. The texture/feature 129C for the haptic structure 120BC may further reduce PCO. Thus, performance of the IOL may be improved.

Figure 4A:
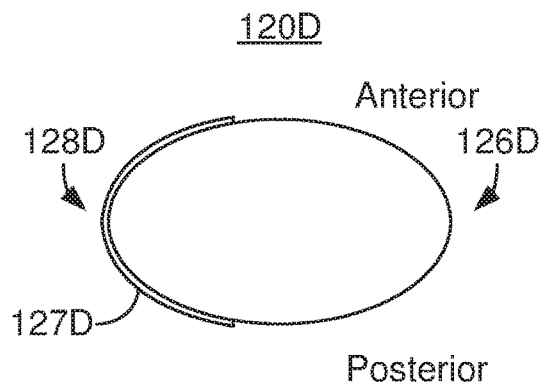
FIGS. 4A-4B depict another exemplary embodiment of a portion of an ophthalmic device having a haptic structure with a cross-section having a streamlined periphery.
Figure 4B:
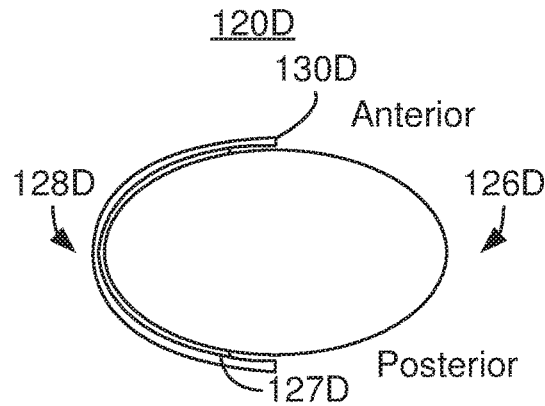

FIGS. 4A and 4B depict another exemplary embodiment of a haptic structure 120D for an ophthalmic device such as an IOL. For clarity, FIGS. 4A and 4B are not to scale and not all components may be shown. FIG. 4A depicts a cross-section of the haptic structure 120D. FIG. 4B depicts the cross-section of the haptic structure 120D when in use, bearing upon the capsular bag 130D of a patient's eye. The haptic 120D and IOL of which it is a part are analogous to the haptic(s) 120A, 120B and/or 120C. Consequently, analogous components have similar labels. Thus, the IOL would include an optic (not explicitly shown) and the haptic structure 120D that are analogous to the optic 110 and haptic structure 120A, 120B and/or 120C. In some embodiments, the haptic structure 120C is a closed-loop haptic structure having loops analogous to the loops 122A, 122B and/or 120C and optionally including a frame analogous to the frame 124A. The frame may be omitted, loop(s) of another size and/or another number of loops may be used. In other embodiments, the haptic structure 120b may have one or more open loops.

The haptic structure 120D functions in an analogous manner to and shares analogous benefits with the haptic structure(s) 120A, 120B and/or 120C. The haptic structure 120D thus includes an outer peripheral surface 128D and an inner peripheral surface 126C that are analogous to surfaces 128A/128B/128C and 126A/126B/126C, respectively. The cross-section of the haptic structure 120D is most analogous to the haptic structure 120C. Instead of having the long axis vertical as in FIGS. 3A and 3B, the long axis is horizontal in FIGS. 4A-4B.

In addition, the haptic structure 120D has a coating 127D. Although shown as residing on only part of the surface of the haptic structure 120D, the coating 127D may cover the entire peripheral surface 128D and 126D. The coating 127D may limit the adherence of the outer peripheral surface 128D to the capsular bag 130D. Thus, the coating 127D may facilitate manipulation or explantation. For example, the coating 127D may include but is not limited to one or more of polyethylene glycol (PEG), plasma and parylene.

The haptic structure 120D may improve performance of an IOL. The streamlined outer peripheral surface 128B of the cross-section may reduce adherence of the haptic structure 120D to the capsular bag 130D during explantation and/or repositioning. The coating 127D may also facilitation repositioning and/or explantation. Thus, damage to the patient's eye due to manipulation of the haptic 120D may be reduced. The smooth curve for the outer peripheral surface 128D may also allow for improved stability of the IOL when the IOL is in place. The texture/feature 127D for the haptic structure 120D may further reduce PCO. Thus, performance of the IOL may be improved.

Figure 5:
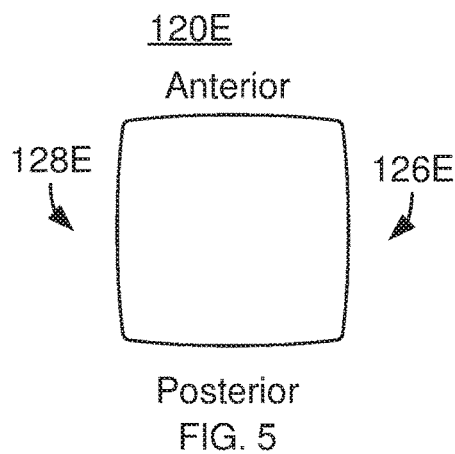
FIG. 5 depicts another exemplary embodiment of a portion of an ophthalmic device having a haptic structure with a cross-section having a streamlined periphery.

FIG. 5 depicts a cross-section of another exemplary embodiment of a haptic structure 120E for an ophthalmic device such as an IOL. For clarity, FIG. 5 is not to scale and not all components may be shown. The haptic 120E and IOL of which it is a part are analogous to the haptic(s) 120A, 120B, 120C and/or 120D. Consequently, analogous components have similar labels. Thus, the IOL would include an optic (not explicitly shown) and the haptic structure 120E that are analogous to the optic 110 and haptic structure 120A, 120B, 120C and/or 120D. In some embodiments, the haptic structure 120E is a closed-loop haptic structure having loops analogous to the loops 122A and optionally including a frame analogous to the frame 124A. The frame may be omitted, loop(s) of another size and/or another number of loops may be used. In other embodiments, the haptic structure 120E may have one or more open loops.

The haptic structure 120E includes an outer peripheral surface 128E and an inner peripheral surface 126E that are analogous to surfaces 128A, 128B, 128C, and 128D and 126A, 126B, 126C and 126D, respectively. However, the shape of the cross-section is different. The cross-section is generally rectangular but has rounded corners and rounded sides. Although all corners are shown as rounded, in some embodiments, one or both corners for the inner peripheral surface 126E may be sharp to mitigate PCO.

The haptic structure 120E may improve patient outcomes. The streamlined outer peripheral surface 128E of the cross-section may reduce adherence of the haptic structure 120E to the capsular bag during explantation and/or repositioning. Thus, damage to the patient's eye due to manipulation of the haptic 120E may be reduced. The smooth curve for the outer peripheral surface 128E may also allow for improved stability of the IOL when the IOL is in place.

Figure 6:
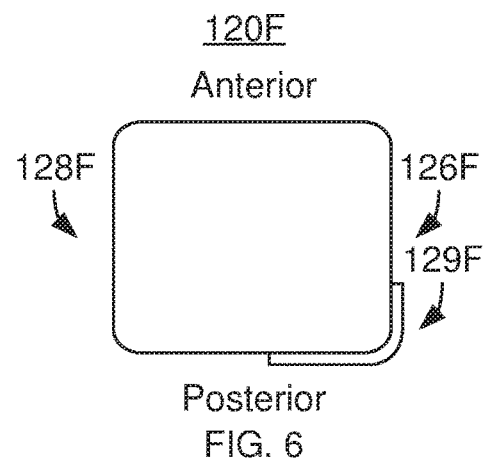
FIG. 6 depicts another exemplary embodiment of a portion of an ophthalmic device having a haptic structure with a cross-section having a streamlined periphery.

FIG. 6 depicts a cross-section of another exemplary embodiment of a haptic structure 120F for an ophthalmic device such as an IOL. For clarity, FIG. 6 is not to scale and not all components may be shown. The haptic 120F and IOL of which it is a part are analogous to the haptic(s) 120A, 120B, 120C, 120D and/or 120E. Consequently, analogous components have similar labels. Thus, the IOL would include an optic (not explicitly shown) and the haptic structure 120F that are analogous to the optic 110 and haptic structure 120A, 120B, 120C, 120D and/or 120E. In some embodiments, the haptic structure 120F is a closed-loop haptic structure having loops analogous to the loops 122A and optionally including a frame analogous to the frame 124A. The frame may be omitted, loop(s) of another size and/or another number of loops may be used. In other embodiments, the haptic structure 120F may have one or more open loops.

The haptic structure 120F includes an outer peripheral surface 128F and an inner peripheral surface 126F that are analogous to outer surfaces 128A, 128B, 128C, 128D and 128E and inner surfaces 126A, 126B, 126C, 126D and 126E, respectively. However, the shape of the cross-section is different. The cross-section is generally rectangular with flat sides but has rounded corners. Although all corners are shown as rounded, in some embodiments, one or both corners for the inner peripheral surface 126F may be sharp to mitigate PCO. The haptic structure 120F also has a coating 129F. Although shown as residing on only part of the surface of the haptic structure 120F, the coating 129F may cover a larger or different area including the entire peripheral surfaces 128F and 126F. The coating 129F may reduce PCO. For example, the coating 129F may include but is not limited to one or more of PEG and Erufosine.

The streamlined outer peripheral surface 128F of the cross-section may reduce adherence of the haptic structure 120F to the capsular bag during explantation and/or repositioning. Thus, damage to the patient's eye due to manipulation of the haptic 120F may be reduced. The smooth curve for the outer peripheral surface 128F may also allow for improved stability of the IOL when the IOL is in place. The coating 129F for the haptic structure 120F may also reduce PCO. Thus, performance of the IOL may be improved.

Figure 7:
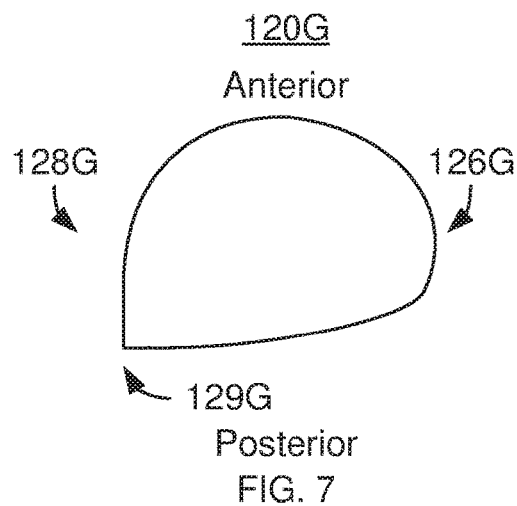
FIG. 7 depicts another exemplary embodiment of a portion of an ophthalmic device having a haptic structure with a cross-section having a streamlined periphery.

FIG. 7 depicts a cross-section of another exemplary embodiment of a haptic structure 120G for an ophthalmic device such as an IOL. For clarity, FIG. 7 is not to scale and not all components may be shown. The haptic 120G and IOL of which it is a part are analogous to the haptic(s) 120A, 120B, 120C, 120D, 120E and/or 120F. Consequently, analogous components have similar labels. Thus, the IOL would include an optic (not explicitly shown) and the haptic structure 120G that are analogous to the optic 110 and haptic structure 120A, 1206, 120C, 120D, 120E and/or 120F. In some embodiments, the haptic structure 120G is a closed-loop haptic structure having loops analogous to the loops 122A and optionally including a frame analogous to the frame 124A. The frame may be omitted, loop(s) of another size and/or another number of loops may be used. In other embodiments, the haptic structure 120G may have one or more open loops.

The haptic structure 120G includes an outer peripheral surface 128G and an inner peripheral surface 126G that are analogous to outer surfaces 128A, 128B, 128C, 128D, 128E and 128F and inner surfaces 126A, 126B, 126C, 126D, 126E and 126F, respectively. However, the shape of the cross-section is different. The cross-section is merely an organic shape having smoothly curved peripheral surfaces 128G and 126G. In addition, the cross-section includes a sharp corner 129G for reducing PCO.

The streamlined outer peripheral surface 128G of the cross-section may reduce adherence of the haptic structure 120G to the capsular bag during explantation and/or repositioning. Thus, damage to the patient's eye due to manipulation of the haptic 120G may be reduced. The smooth curve for the outer peripheral surface 128G may also allow for improved stability of the IOL when the IOL is in place. The coating 129G for the haptic structure 120G may also reduce PCO. Thus, performance of the IOL may be improved.

Figure 8:
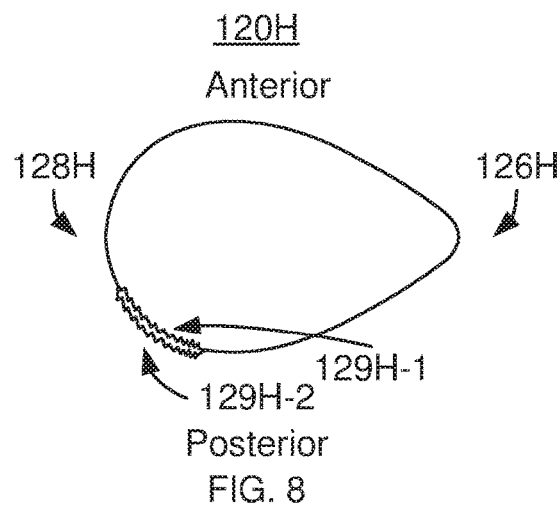
FIG. 8 depicts another exemplary embodiment of a portion of an ophthalmic device having a haptic structure with a cross-section having a streamlined periphery.

FIG. 8 depicts a cross-section of another exemplary embodiment of a haptic structure 120H for an ophthalmic device such as an IOL. For clarity, FIG. 8 is not to scale and not all components may be shown. The haptic 120H and IOL of which it is a part are analogous to the haptic(s) 120A, 120B, 120C, 120D, 120E, 120F and/or 120G. Consequently, analogous components have similar labels. Thus, the IOL would include an optic (not explicitly shown) and the haptic structure 120H that are analogous to the optic 110 and haptic structure 120A, 120B, 120C, 120D, 120E, 120F and/or 120G. In some embodiments, the haptic structure 120H is a closed-loop haptic structure having loops analogous to the loops 122A and optionally including a frame analogous to the frame 124A. The frame may be omitted, loop(s) of another size and/or another number of loops may be used. In other embodiments, the haptic structure 120H may have one or more open loops.

The haptic structure 120H includes an outer peripheral surface 128H and an inner peripheral surface 126H that are analogous to outer surfaces 128A, 128B, 128C, 128D, 128E, 128F and 128G and inner surfaces 126A, 126B, 126C, 126D, 126E, 126F and 126G, respectively. However, the shape of the cross-section is different. The cross-section is a tear drop shape analogous to that of the haptic structure 120A. However, the corner 129A has been rounded. Although the sides of the inner peripheral surface 126H are shown as rounded (i.e. convex), in other embodiments, the sides might be flat or concave.

The haptic structure 120H also includes a texture or features 129H-1 and a coating 129H-2 on the texture/feature 129H-1. The texture/feature 129H-1 may be analogous to the texture/feature 129C. The coating 129H-2 may be analogous to the coating 127D or 129F. Thus, the coating 129H-2 may reduce PCO. The coating 129H-2 might be used to facilitate explantation or manipulation of the haptic structure 120H.

The streamlined outer peripheral surface 128H of the cross-section may reduce adherence of the haptic structure 120H to the capsular bag during explantation and/or repositioning. Thus, damage to the patient's eye due to manipulation of the haptic 120H may be reduced. The smooth curve for the outer peripheral surface 128H may also allow for improved stability of the IOL when the IOL is in place. The texture/feature 129H-1 may mitigate PCO. The coating 129H-2 for the haptic structure 120H may also reduce PCO or may facilitate explantation or repositioning. Thus, performance of the IOL may be improved.

Figure 9:
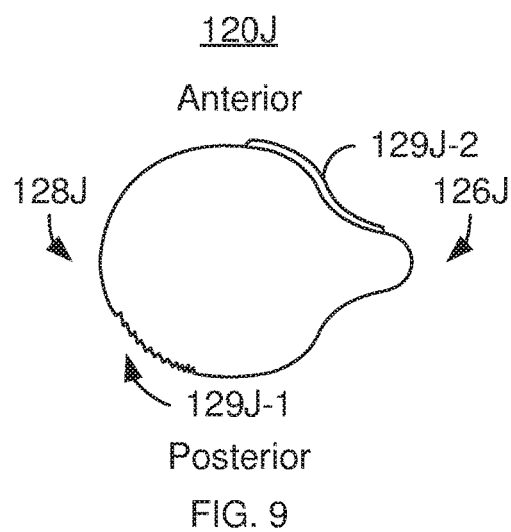
FIG. 9 depicts another exemplary embodiment of a portion of an ophthalmic device having a haptic structure with a cross-section having a streamlined periphery.

FIG. 9 depicts a cross-section of another exemplary embodiment of a haptic structure 120J for an ophthalmic device such as an IOL. For clarity, FIG. 9 is not to scale and not all components may be shown. The haptic 120J and IOL of which it is a part are analogous to the haptic(s) 120A, 120B, 120C, 120D, 120E, 120F, 120G and/or 120H. Consequently, analogous components have similar labels. Thus, the IOL would include an optic (not explicitly shown) and the haptic structure 120J that are analogous to the optic 110 and haptic structure 120A, 120B, 120C, 120D, 120E, 120F, 120G and/or 120H. In some embodiments, the haptic structure 120J is a closed-loop haptic structure having loops analogous to the loops 122A and optionally including a frame analogous to the frame 124A. The frame may be omitted, loop(s) of another size and/or another number of loops may be used. In other embodiments, the haptic structure 120J may have one or more open loops.

The haptic structure 120J includes an outer peripheral surface 128J and an inner peripheral surface 126J that are analogous to outer surfaces 128A, 1286, 128C, 128D, 128E, 128F, 128G and 128H and inner surfaces 126A, 126B, 126C, 126D, 126E, 126F, 126G and 126H, respectively. However, the shape of the cross-section is different. The cross-section is generally a tear drop shape analogous to that of the haptic structures 120A and 120H. The corner 129A has been rounded. In addition, the sides of inner peripheral surface 126J are concave rather than straight or convex.

The haptic structure 120J also includes a texture or features 129J-1 and a coating 129J-2. The texture/feature 129J-1 may be analogous to the texture/feature(s) 129C and 129H-1. The texture/feature 129J-1 may thus mitigate PCO. The coating 129J-2 may be analogous to the coating 127D or 129F. The coating 129J-2 is also located on the anterior side. The coating 129J-2 may reduce PCO and/or reduce adherence of the haptic structure 120J to the capsular bag when the haptic structure 120J is being manipulated.

The smooth curve of the outer peripheral surface 128J of the cross-section may reduce adherence of the haptic structure 120J to the capsular bag during explantation and/or repositioning. Thus, damage to the patient's eye due to manipulation of the haptic 120J may be reduced. The smooth curve for the outer peripheral surface 128J may also allow for improved stability of the IOL when the IOL is in place. The texture/feature 129J-1 may mitigate PCO. The coating 129J-2 for the haptic structure 120J may also reduce PCO or may facilitate explantation or repositioning. Thus, performance of the IOL may be improved.

Figure 10:
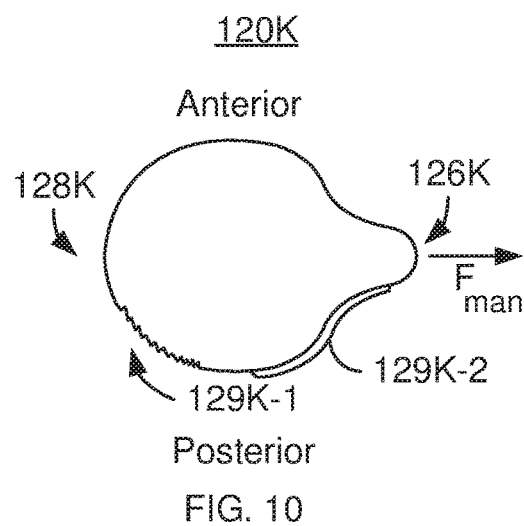
FIG. 10 depicts another exemplary embodiment of a portion of an ophthalmic device having a haptic structure with a cross-section having a streamlined periphery.

FIG. 10 depicts a cross-section of another exemplary embodiment of a haptic structure 120k for an ophthalmic device such as an IOL. For clarity, FIG. 10 is not to scale and not all components may be shown. The haptic 120k and IOL of which it is a part are analogous to the haptic(s) 120A, 120B, 120C, 120D, 120E, 120F, 120G, 120H and/or 120J. Consequently, analogous components have similar labels. Thus, the IOL would include an optic (not explicitly shown) and the haptic structure 120K that are analogous to the optic 110 and haptic structure 120A, 120B, 120C, 120D, 120E, 120F, 120G, 120H and/or 120J. In some embodiments, the haptic structure 120K is a closed-loop haptic structure having loops analogous to the loops 122A and optionally including a frame analogous to the frame 124A. The frame may be omitted, loop(s) of another size and/or another number of loops may be used. In other embodiments, the haptic structure 120K may have one or more open loops.

The haptic structure 120K includes an outer peripheral surface 128K and an inner peripheral surface 126K that are analogous to outer surfaces 128A, 128B, 128C, 128D, 128E, 128F, 128G, 128H and 128J and inner surfaces 126A, 126B, 126C, 126D, 126E, 126F, 126G, 126H and 126J, respectively. The cross-section of the haptic 120K matches that of the haptic structure 120J. The haptic structure 120K also includes a texture/features 129K-1 and a coating 129K-2 that are analogous to the texture/features 129J-1 and 129J-2, respectively. However, the coating 129K-2 is also located on the posterior side away from the texture/feature 129K-1.

The smooth curve of the outer peripheral surface 128K of the cross-section may reduce adherence of the haptic structure 120K to the capsular bag during explantation and/or repositioning. Thus, damage to the patient's eye due to manipulation of the haptic 120K may be reduced. The smooth curve for the outer peripheral surface 128K may also allow for improved stability of the IOL when the IOL is in place. The texture/feature 129K-1 may mitigate PCO. The coating 129K-2 for the haptic structure 120K may also reduce PCO or may facilitate explantation or repositioning. Thus, performance of the IOL may be improved.

Various features of the haptic structures 120A, 120B, 120C, 120D, 120E, 120F, 120G, 120H, 120J and 100K have been described herein. One of ordinary skill in the art will recognize that one or more of these features may be combined in manners not explicitly disclosed herein and that are not inconsistent with the method and apparatus described. Further, as discussed above, the dimensions and/or aspect ratios of each embodiment may vary. Thus, the appearance of the cross-section may differ in different embodiments. In addition, individual features of different embodiments may be combined. For example, different quadrants shown in the cross-sections of different embodiments may be combined to form a new embodiment. Further, there is no requirement that the cross-section exhibit symmetry, such as symmetry around a horizontal axis, a vertical axis and/or an oblique axis.

Figure 11A:
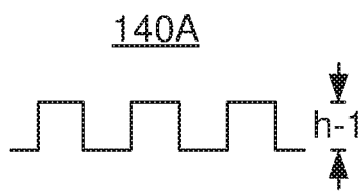
FIGS. 11A-11C depict exemplary embodiments of textures/patterns that may be used on the haptic structure with a cross-section having a streamlined periphery.
Figure 11B:
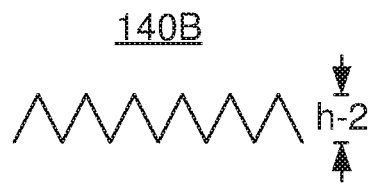
Figure 11C:
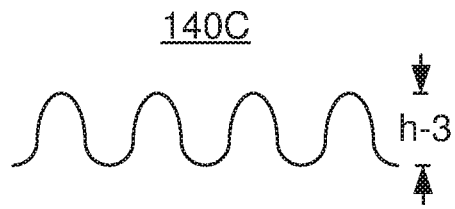

FIGS. 11A, 11B and 11C depict various embodiments of textures and/or features that might be used for one or more of the textures/features 129C, 129H-1, 129J-1 and 129K-1. FIG. 11A depicts textures/features 140A having height h-1. FIG. 11B depicts textures/features 140B having height h-2. FIG. 11C depicts textures/features 140C having height h-3. The textures/features 140A have a square profile and might be seen as a series of lines. Textures/features 140B are a saw tooth having characteristic height h-2. Textures/features 140C may be viewed as lines or steps but have curved edges. For heights h-1, h-2 and h-3 not larger than the order of nanometers to microns, items 140A, 140B and 140C may be considered textures. For heights h-1, h-2 and h-3 on the order of tens of microns or more, items 140A, 1406 and 140C are features. However, the heights h-1, h-2 and h-3 are significantly less than the radius of curvature of the cross section of the haptics. Further, although specific patterns and constant heights are shown in FIGS. 11A-11C, the textures/features 140A, 1406 and 140C may have varying height(s), width(s) and/or pitch(es). Further, at the smaller scales, the textures/features 140A, 1406 and/or 140C may simply be viewed as a roughening of the surface of the haptic. For the scales described above the textures/features 140A, 1406 and 140C may aid in reducing PCO.

It will be appreciated that various of the above-disclosed and other features and functions, or alternatives thereof, may be desirably combined into many other different devices or applications. It will also be appreciated that various presently unforeseen or unanticipated alternatives, modifications, variations or improvements therein may be subsequently made by those skilled in the art which alternatives, variations and improvements are also intended to be encompassed by the following claims.

We claim:

1. An ophthalmic device comprising:
an optic including an optic axis extending through an anterior surface and a posterior surface of the optic in a substantially perpendicular direction, wherein the optic is configured such that the optic axis extends substantially parallel to an optical axis of an eye when implanted into the eye; and
a haptic structure coupled with the optic and for retaining the ophthalmic device within a capsular bag of the eye, at least a portion of the haptic structure having a cross-section comprising a tear drop shape and spanning in a direction substantially parallel to the optic axis, the cross-section comprising a continuously-curved outer peripheral surface extending along the direction of the optic axis for contacting the capsular bag, the cross-section further comprising an inner peripheral surface having concave sides on opposing ends of a rounded corner, and wherein the at least a portion of the haptic structure subtends an angle of at least 90 degrees around the optic.

2. The ophthalmic device of claim 1, wherein the haptic structure includes at least one of a texture for reducing posterior capsular opacification (PCO), a feature for reducing PCO, a first coating for reducing PCO and a second coating on at least a portion of the peripheral surface for reducing adherence of the haptic structure to the capsular bag.

3. The ophthalmic device of claim 1, wherein the haptic structure is a closed-loop haptic structure.

4. The ophthalmic device of claim 1, wherein the haptic structure includes a texture for reducing posterior capsular opacification (PCO).

5. The ophthalmic device of claim 1, wherein the haptic structure includes a first coating for reducing posterior capsular opacification (PCO).

6. The ophthalmic device of claim 1, wherein the haptic structure includes a first coating for reducing posterior capsular opacification (PCO) and a second coating on at least a portion of the peripheral surface for reducing adherence of the haptic structure to the capsular bag.

7. The ophthalmic device of claim 1, wherein the haptic structure comprises two closed loops, and wherein the two closed loops together subtend an angle of at least 120 degrees around the optic.

8. An ophthalmic device comprising:
An optic including an optic axis extending through an anterior surface and a posterior surface of the optic in a substantially perpendicular direction, wherein the optic is configured such that that optic axis extends substantially parallel to an optical axis of an eye when implanted into the eye; and
a closed-loop haptic structure coupled with the optic and for retaining the ophthalmic device within a capsular bag of the eye, at least a portion of the closed-loop haptic structure having a cross-section comprising a tear drop shape and spanning in a direction substantially parallel to the optic axis, the cross-section comprising a continuously-curved outer peripheral surface extending along the direction of the optic axis, the cross-section further comprising an inner peripheral surface having concave sides on opposing ends of a rounded corner, and wherein:
the outer peripheral surface is for contacting the capsular bag;
the at least a portion of the closed-loop haptic structure subtends an angle of at least 90 degrees around the optic; and
the closed-loop haptic structure includes at least one of a texture for reducing posterior capsular opacification (PCO), a sharp edge for reducing PCO, a feature for reducing PCO, a first coating for reducing PCO and a second coating on at least a second portion of the peripheral surface for reducing adherence of the haptic structure to the capsular bag.

9. The ophthalmic device of claim 8, wherein the closed-loop haptic structure comprises two closed loops, and wherein the two closed loops together subtend an angle of at least 120 degrees around the optic.

* * * * *